D. D. Parmelee,
Artificial Leg.
No. 1,908. Reissued Mar. 21, 1865.
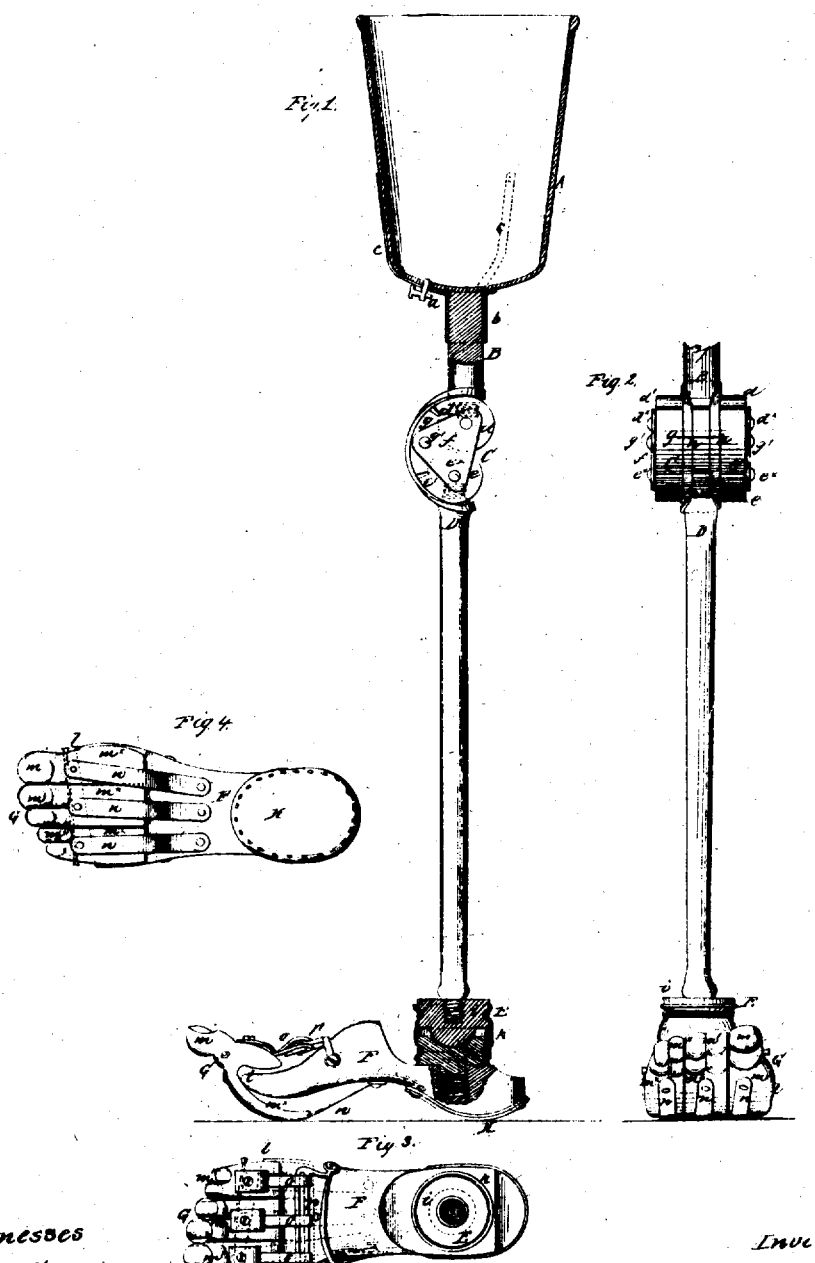
Witnesses
Jno. T. Shine
M. J. Pastrick
Inventor.
Daniel D. Parmelee

UNITED STATES PATENT OFFICE.

DUBOIS D. PARMELEE, OF NEW YORK, N. Y.

IMPROVEMENT IN ARTIFICIAL LEGS.

Specification forming part of Letters Patent No. 37,637, dated February 10, 1863; Reissue No. 1,998, dated March 21, 1865.

DIVISION B.

*To all whom it may concern:*

Be it known that I, DUBOIS D. PARMELEE, of the city, county, and State of New York, have invented certain new and useful Improvements in Artificial Limbs; and I do hereby declare that the following is a full, clear, and exact description of the same, reference being had to the accompanying drawings, forming a part of this specification, in which—

Figure 1 represents a sectional side elevation of a leg constructed according to my invention. Fig. 2 is a front view of the same. Fig. 3 is a horizontal section of the same, taken in the plane indicated by the line *x x*, Fig. 1. Fig. 4 is an inverted plan of the same.

Similar letters of reference in the three views indicate corresponding parts.

The great difficulty and expense attending the manufacture of artificial limbs consists in properly shaping and fitting the bucket or socket onto the stump, for unless the stump be snugly housed and fitted in the bucket it is liable to become chafed and inflamed, and thus cause intolerable pain to the wearer, but particularly in buckets which, according to my invention, are held in lieu of straps or other mechanical fastenings by means of atmospheric pressure, it is necessary and essential that as perfect a fit as possible should be obtained. Heretofore the buckets were made of a certain description of wood to fit which repeated trials or "sittings" were necessary to enable the artisan to scrape away particles of wood in conformity with the shape of the stump. This tentative mode of making the buckets requires great skill on the part of the operator, is very laborious and expensive, and renders it impossible to produce artificial limbs on a manufacturing scale.

The object of this invention, therefore, is to make buckets of a material and in a manner such as will allow of its being made with perfect accuracy in conformity with the shape of the stump, and to this effect my said invention consists, first, in the method of making the bucket of artificial limbs of a plastic substance capable of being subsequently indurated on a mold or cast of the stump, in the manner and for the purpose set forth; secondly, in shaping the interior of buckets when made of a substance rendered plastic by heat by means of a core which is the fac-simile of the stump, in combination with the requisite degree of heat, substantially in the manner and for the purpose set forth; thirdly, in the manufacture of artificial limbs with buckets of hard rubber or vulcanite, or its equivalent, for holding the stump, substantially as described.

To enable those skilled in the art to make and use my invention, I will proceed to describe the construction and operation of a leg to which my improvements are applied, and, referring to the drawings—

A represents the bucket or socket or receptacle of the stump of the amputated limb. The process by which this bucket is formed is somewhat similar to that by which dentists form plates of hard rubber to conform perfectly to the roof of the mouth to be held there by atmospheric pressure. A form or mold of the stump is prepared in wax, plaster-of-paris, (if of plaster-of-paris the inside of the mold should be oiled,) or gutta-percha may be employed. Into this mold plaster-of-paris or fusible metal is cast, and thereby a perfect fac-simile or form of the natural stump is obtained. Around this form a sheet of india-rubber or gutta-percha compound prepared for hard vulcanization is tightly wound and made to snugly conform to said form. The whole is then firmly bound with wetted cloths or embedded in plaster-of-paris, and thus prepared it is placed in the heater and vulcanized. After the vulcanization is completed the bucket is taken out and polished and mounted, as will be presently described.

Instead of this mode of obtaining the bucket, the following process may be found practicable: A hollow cone of vulcanite is formed, the inner circumference of which is the measurement of the stump to be fitted. A form or fac simile of the stump is next taken, as above described. The hollow cone is heated to 212° Fahrenheit, or more, if necessary, and forced over the form of the stump and allowed to cool upon it. The form is next broken out if of plaster, or if of fusible metal the whole is embedded in plaster-of paris, and then the metal melted out by immersion in oil or other liquid capable of sustaining the required temperature. The bucket may thus be made to perfectly fit the stump. It may be provided with an air-valve, *a*, so that on placing the stump into the bucket with the air-valve open the air shall be expelled from the bucket. If after setting the stump the valve be closed, the pressure of the atmosphere will hold the bucket in its place till air is readmitted.

To obviate inconvenience from insensible perspiration, a dry sponge, cotton, wool, or small bag of fused chloride of calcium may be placed at the bottom of the bucket. This bucket is fastened to that part representing the thigh bone or femur B, when used for a leg amputated above the knee, by a metal ferrule, *b*. From this ferrule project three or more metal bands, *c*, which are riveted to the bucket. By this arrangement it is perfectly easy to adjust the length of the limb with utmost accuracy, simply by shifting the ferrule *b* up or down on the artificial thigh-bone B until the bucket has attained the required position.

C is the knee-joint, which is formed of two cylinders, *d* and *e*, one being fastened to the lower end of the artificial thigh-bone B, and the other to the upper end of the artificial large bone of the leg or tibia D. Each of these cylinders is provided with a lip or offset, *d′ e′*, and they rotate respectively on axles *d** and *e**, which have their bearings in metallic side clasps, *f*. A double concave sector, *g*, is located between the cylinders *d e*, being retained in its place by pivots *g′*, passing through the clasps *f*. The concave sides of this sector, which fit the surfaces of the cylinders *d e*, form the artificial knee-pan, and its edges, by coming in contact with the lips or off sets *d′ e′*, confine the motion of the joint within the desired limits. An india-rubber band, *h*, which is stretched over the convex surface of the knee-pan, and around the supports B D, has a tendency to straighten the leg and unbend the knee, thereby assisting the movement of the foot forward while walking, giving at the same time uniform elasticity to the artificial knee-pan. By the movement of the joint the cylinder *d* rolls over the surface of the lower one, *e*, and the friction thus created is greatly reduced. The heel or ankle joint E is here shown as formed of two pieces, *i j*, one of which is provided with a semi-spherical socket and the other with a corresponding projection or ball. This ball should accurately fit the socket, and each of the two pieces *i j* is provided with flanges, whereby the movement or play of said parts in either direction is confined between limits such as may be desired. The upper part, *i*, of the heel joint is fastened to the lower end of the artificial tibia, and the lower part, *j*, of said joint is screwed or otherwise firmly secured to the foot-piece F, and the two parts *i j* are fastened together by an india-rubber tube, *k*, of proper thickness and strength, which is stretched over both, and secured to each by a cord or in any other desirable manner. The foot-piece F corresponds in form to the bones of the instep and heel-bone of the natural foot. Its front end, *l*, is rounded off and forms the fulcrum for the toe-piece G. The latter is divided into three (more or less) distinct parts, *m m′ m″*, one of which corresponds to the large toe and each of the others to two of the other toes. These toe-pieces are held in place by bands *n*, of leather or other inelastic but flexible material, fastened by means of screws or any other desirable means to the under side of both the toe and the foot piece, and by elastic bands *o*, of india-rubber or any other suitable yielding material, fastened in any convenient manner to the upper surface of both the toe-pieces and the foot-piece. The inner ends of the elastic bands *o* pass through a metal clasp, *p*, so as to admit tightening or loosening according to the requisite rigidity in the play of the toes. By the action of these elastic bands or springs the points of the toes are thrown up so as to prevent interference when bringing the foot forward, and their position is regulated by the length of the leather bands *n*, which bear against the stems or tails *m**, extending from the toe-pieces *m m′ m″* below the point of the foot-piece F, as shown in Fig. 1 of the drawings. If the weight of the body is upon the front of the foot, by the action of the tails *m** the toe-pieces are turned down and a large base is attained, thereby enabling the person wearing the leg to maintain his or her balance with little labor. The toes, by being divided, are capable of adapting themselves to the inequalities of the ground. The heel H is covered with an elastic pad to prevent jarring in the act of walking. The case for this leg or arm may be made of cork, papier-maché, or any other suitable material, but I would recommend a leather tube, cut into the shape of the limb, sewed up, and small hoops of steel springs placed and fastened on the interior at about three inches apart to give form to the case, and at the same time preserve its flexibility. Such a case might be fastened by hooks to the bucket at the top, and when used for a leg be made to connect at the bottom with the boot or shoe inclosing the foot.

The principal advantages of my artificial limb are that it can be fastened to the stump without the use of straps around the waist or shoulder, and it requires no tedious fitting; but I desire it to be understood that I do not confine my invention as applied to buckets made to be attached to the stump by atmospheric pressure, but I deem it a valuable invention in connection with any artificial limb, of whatsoever construction, as facilitating, expediting, cheapening, and rendering more perfect the construction of buckets.

Having now fully described my said invention, what I claim as new, and desire to secure by Letters Patent, is—

1. The method of making the bucket of artificial limbs of a plastic substance capable of being subsequently indurated upon a mold or cast of the stump, in the manner and for the purpose set forth.

2. Shaping the interior of buckets when made of a substance rendered plastic by heat by means of a core, which is the fac-simile of the stump, in combination, with the requisite degree of heat, substantially in the manner and for the purpose set forth.

3. The manufacture of artificial limbs, with buckets of hard rubber or vulcanite, or its equivalent, for holding the stump, substantially as described.

In testimony whereof I have signed my name to this specification before two subscribing witnesses.

D. D. PARMELEE.

Witnesses:
T. A. WHITAKERS,
THOS. A. GERE.